United States Patent
Beier (10) Patent No.: US 6,582,917 B1
(45) Date of Patent: Jun. 24, 2003

(54) METHOD FOR CONTROLLING QUALITY IN THE CONSTRUCTION OF OLIGOMER GRIDS

(75) Inventor: Markus Beier, Heidelberg (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 0 days.

(21) Appl. No.: 09/787,226

(22) PCT Filed: Sep. 15, 1999

(86) PCT No.: PCT/DE99/02975

§ 371 (c)(1),
(2), (4) Date: Jun. 22, 2001

(87) PCT Pub. No.: WO00/15837

PCT Pub. Date: Mar. 23, 2000

(30) Foreign Application Priority Data

Sep. 15, 1998 (DE) .......................................... 198 42 164

(51) Int. Cl.[7] ................................................ C12Q 1/68
(52) U.S. Cl. .......................... 435/6; 435/7.1; 435/91.1; 435/91.2; 435/287.2; 536/22.1; 536/23.1; 536/4.1; 536/24.3; 536/24.31; 536/26.6
(58) Field of Search .................... 435/6, 7.1, 91.1, 435/91.2, 287.2; 536/22.1, 23.1, 24.3–24.33, 4.1, 26.6

(56) References Cited

U.S. PATENT DOCUMENTS 5,231,191 A * 7/1993 Woo et al.
6,174,998 B1 * 1/2001 Muhlegger et al. .......... 536/4.1

FOREIGN PATENT DOCUMENTS

| DE | 196 25 397 A1 | 1/1998 |
| EP | 475 443 A | 3/1992 |
| EP | 0 818 460 A2 | 1/1998 |
| WO | WO 94/08047 | 4/1994 |
| WO | WO 97/39151 | 10/1997 |

OTHER PUBLICATIONS

Weiler J., et al; *Combining the Preparation of Oligonucleotide Arrays and Synthesis of High–Quality Primers*; Analytical Biochemistry, U.S., Academic Press, San Diego, CA; vol. 243, No. 2, pp. 218–227; (Dec. 15, 1996).

Weiler J., et al., *Picomole Syntheses of High Quality Oligonucleotide Primers in Combination with the Preparation of Oligonucleotide Arrays;* Nucleosides & Nucleotides, vol. 16, Nos. 7–9; pp. 1793–1796; (1997).

* cited by examiner

Primary Examiner—Jeffrey Siew
(74) Attorney, Agent, or Firm—Albert P. Halluin; Viola T. Kung; Howrey, Simon, Arnold & White, LLP (57) ABSTRACT

The present invention relates to a method for controlling the quality of oligomer arrays, which is characterized in that a phosphate unit is fused to certain array positions, said phosphate unit being linked to a signal-generating reporter group, the degree of oligomer synthesis is determined using the signal of the reporter group, and the reporter group is then split off again.

6 Claims, 6 Drawing Sheets

METHOD FOR CONTROLLING QUALITY IN THE CONSTRUCTION OF OLIGOMER GRIDS

This application is a National Stage of International Application PCT/DE99/02975, filed Sep. 15, 1999; which claims the priority of DE 198 42 164.8, filed Sep. 15, 1998.

BACKGROUND OF THE INVENTION

The invention relates to a method for controlling the quality in the construction of oligomer arrays.

For diagnostic screenings microchips are coated with oligomers in the form of arrays (oligomer chips/biochips). A sample can then be screened therewith for a suitable molecule, i.e. a molecule hybridizing therewith. Such oligomer arrays on a chip may comprise nucleic acid oligonucleotides, such as DNA, RNA or nucleic acid biopolymers, or analog compounds thereto, which are applied to a solid phase.

The oligomers are not always fixed quantitatively, so that it is not always possible to obtain chips having the same coating degree. Following the construction of such oligomer arrays it must therefore be checked whether the synthesis was successful and/or the degree of successful synthesis must be determined. For this purpose, phosphate reagents provided with a permanent (fluorescent) label have been used thus far. Since these labels could not be split off again, they optionally impair the subsequent use of the biochips.

A defined quality assay for the construction of oligomer arrays on a chip surface which does not trigger any disturbing side-effects is thus not known as yet. However, a quality control is inevitable in the developing field of biochip technology to, ensure a reproducible production of constant quality.

BRIEF SUMMARY OF THE INVENTION

It is the object of this invention to provide a method for controlling the quality of oligomer arrays. It shall be possible to use this method universally and carry it out rapidly and with little effort. In addition, the quality control shall not impair the subsequent use as a biochip. The method shall be suitable for all kinds of oligomer arrays.

This object is achieved by a method according to claim 1. Advantageous embodiments follow from the subclaims.

DETAILED DESCRIPTION OF THE INVENTION

It has been found surprisingly that a quality control without impairing the further use of the chip can be carried out when a phosphate unit is fused to the oligomer grid on the chip, which is reversibly provided, or connected, with a signal-generating reporter group. By the detection of the signal from the reporter group attached to the oligomers at the grid positions it is possible to control the success of the synthesis or to compare different grid positions with one another. Having concluded the quality control, the reporter group is removed again.

Figure 5:
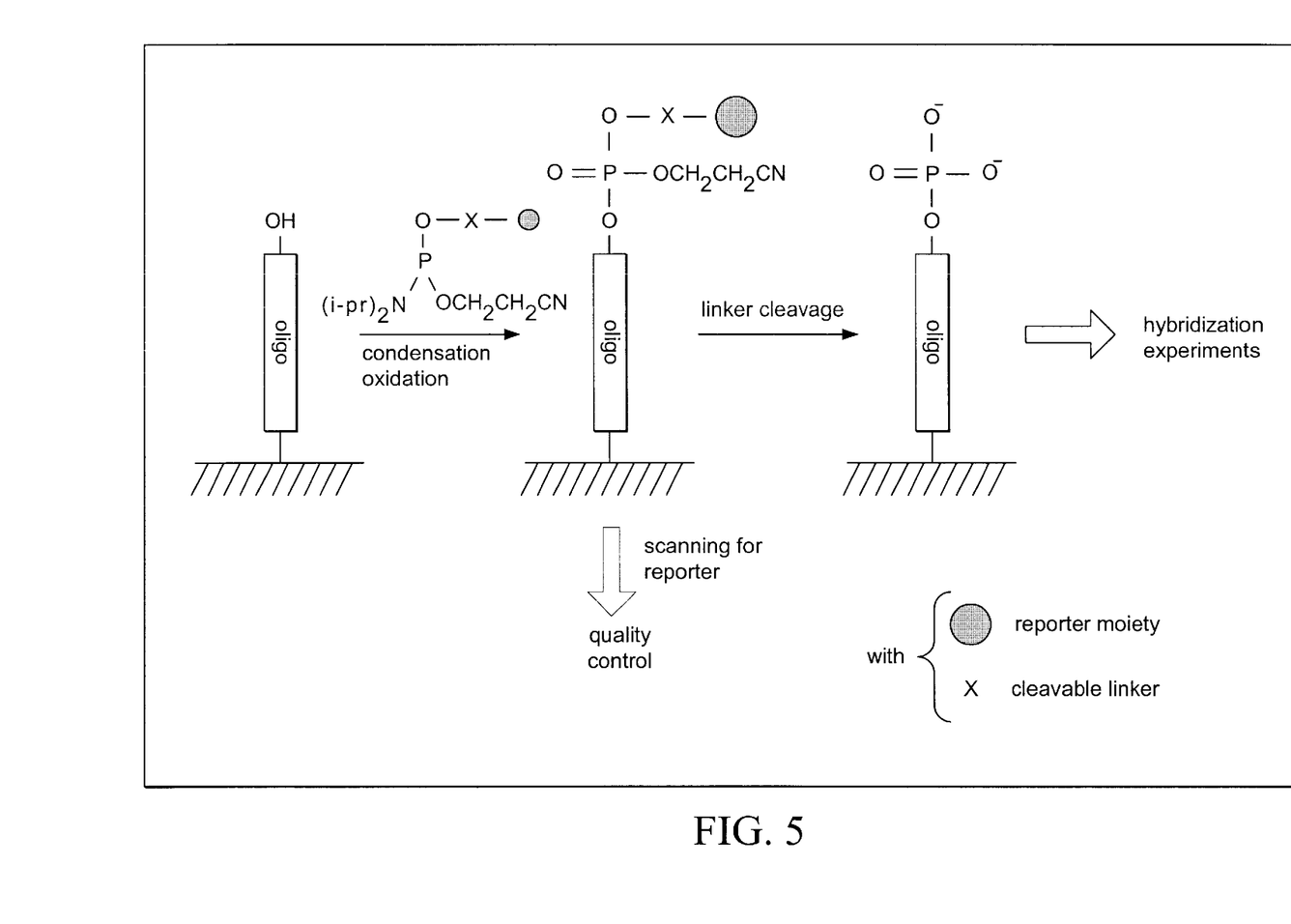
FIG. 5 shows the scheme of the method according to the invention (1-step method).
Figure 6:
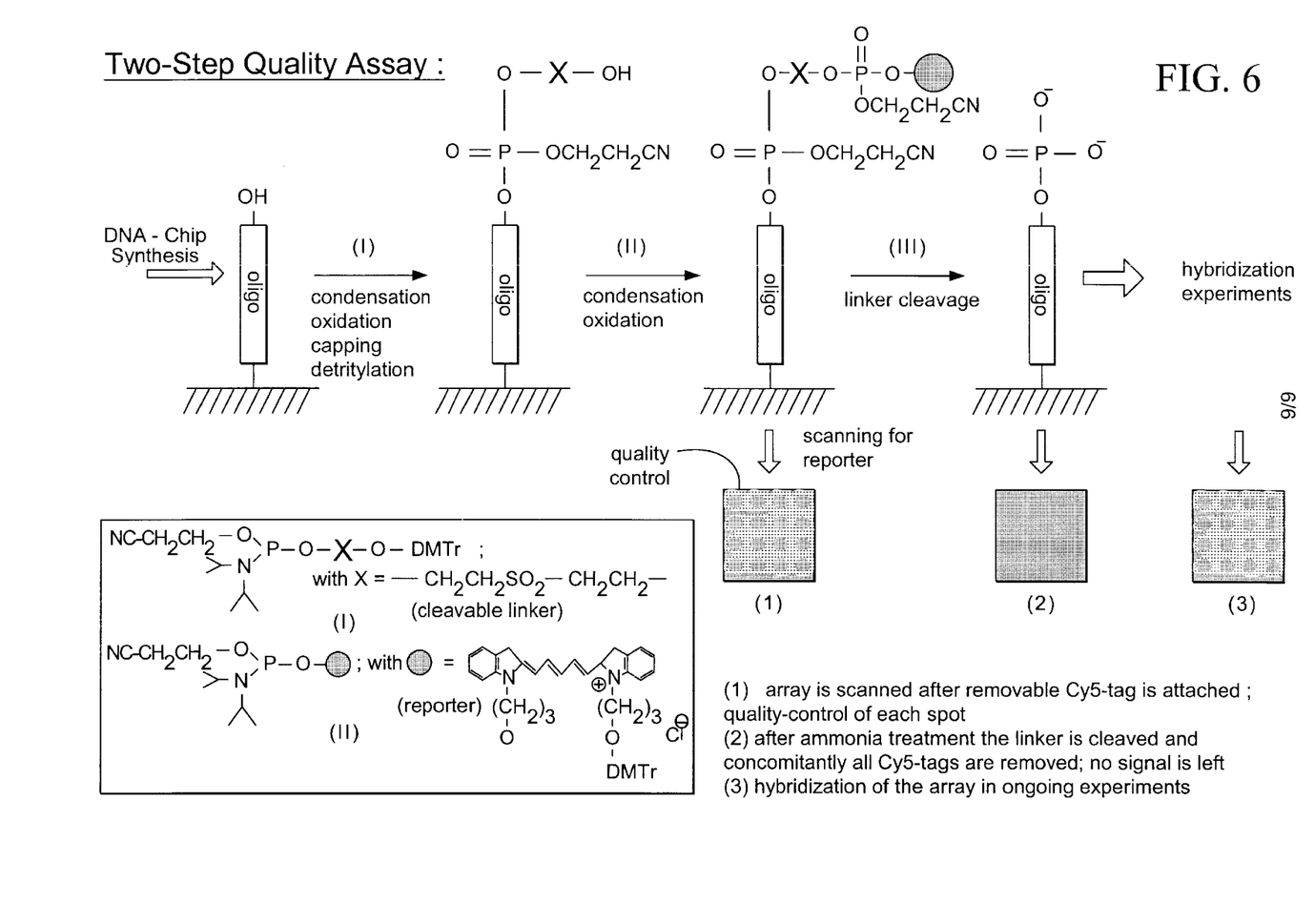
FIG. 6 shows the scheme of the method according to the invention (2-step method).

Thus, the invention relates to a method for controlling the quality of oligomer arrays, which is characterized in that a phosphate unit linked to a signal-generating reporter group is fused to oligonucleotides at certain grid positions (preferably to all or a previously selected number), the degree of oligomer synthesis is determined by means of the signal of the reporter group, and the reporter group is then split off again. A general scheme is shown in FIGS. 5 and 6.

The extent of the synthesis success can be controlled by detecting the reporter group signals emitted from the occupied grid positions. Having concluded the quality control, the reporter group can be split off again and in this way that does not cause any disturbing effects in the subsequent experiments. Only the phosphate group remains attached to the oligomers. However, it does not disturb the subsequent use, e.g. in a hybridization, but optionally increases advantageously the melting temperature of the oligomer bound to the solid phase.

According to the invention, a phosphate unit is understood to mean a unit fused using methods of the phosphoramidite chemistry. The phosphate units may also be produced by methods known from the phosphomonoester, phosphodiester or H-phosphonate chemistry.

The invention is described below by means of phosphoramidite as a basis of the phosphate group, which is preferred according to the invention. However, this should not be interpreted as a limitation. According to the invention the phosphate unit is produced by reaction of the oligomer already disposed at the solid phase at its 5' or 3' end with the phosphoramidite after the oxidation. Here, the phosphoramidite is reacted using an acidic catalyst (e.g. tetrazole, tetrazole derivatives, pyridine hydrochloride) with the oligomer strand disposed at the solid phase. Subsequent oxidation, e.g. using iodine, tert.-butylhydroperoxide, etc., results in a stable phosphorus(V) compound (=phosphate unit). It proves to be advantageous that it is possible to use in this case the steps common for the synthesis of oligonucleotides, which can be automated without any problems on a commercially available DNA/RNA synthesizer. No modifications of the commonly used reagents or synthesis protocols are necessary for this purpose.

The signal-generating reporter group may be any signal-generating molecule which can be coupled to a phosphoramidite via a corresponding linker. The linker takes care that after the reaction of the phosphoramidite with the oligomer on the solid phase and after the detection of the reporter group, the reporter group can be split off. Signal-generating reporter groups may be any fluorescent, coloring, radioactive, chemoluminescent compounds. Fluorescent compounds are preferred, such as dansyl ethanol, fluorescein or pyrene. Examples of further reporter groups are derivatives of Cy3, Cy5, dabsyl chloride, TAMRA, hexachlorofluorescein, suitably derivatized for coupling to the phosphate group. According to the invention the reporter group may already be linked to the phosphate unit when the latter is bound to the oligomer (1-step process, see FIGS. 1 and 5) or the linker may be bound by means of a phosphate unit to the oligomer before the reporter group is attached using another phosphate unit (2-step process, see FIG. 6).

The 1-step process is explained in detail in Example 1. It is characteristic of the 1-step process that the reporter molecule (e.g. fluorescence tag) and the cleavable linker form parts of a single chemical molecule (e.g. 2-cyanoethyl-2-danyslethyl-N,N-diisopropyl phosphoramidite). It is fused to the chip during the last step of the oligonucleotide synthesis. Following the oxidation to form a stable phosphodiester, the chip is checked using the detection of the reporter group for its quality. Thereafter, the reporter group is removed e.g. by base treatment. The phosphate protecting groups may be removed preferably, but not necessarily, in the same step or later. A phosphate unit is left as an attachment at one end of the respective oligomer strand. The array can then be used in standard experiments (e.g. in hybridizations).

In the 1-step process, the linker contains a unit which can be split off by an acid, base or by light (hereinafter: X), e.g. sulfonylethyl, 2-(2,2-dicarboxyethyl)propyl, 2-(2-nitrophenyl)propyl, 2-(2-nitrophenyl)ethyl. Furthermore, the linker contains a hydroxy or amino function (hereinafter: H) for the attachment of the signal-generating reporter group. The linker also contains a spacer (hereinafter: M) which spatially separates the cleavable unit (X) from the amino or hydroxyl function (H). The linker (L) may therefore be represented by the following general formula:

wherein
X=cleavable unit
H=hydroxyl or amino
M=alkyl, aryl, etc.

Prior to the condensation to the oligomer array, a reagent is formed in which the linker is connected with a phosphite amide unit and with the reporter group. The reporter group is linked by means of suitable reporter derivatives. Linkages to the hydroxy or amino function (H) via an ester or amide or sulfonamide bridge are preferred, since commercially suitable derivatized compounds (e.g. carboxylic acids, sulfonyl chlorides) of almost all known reporter groups are available for this. The reagent has the following general formula:

L = cleavable linker unit
$R^1$ = phosphate protecting group, e.g. á-cyanoethyl, 2-(4-nitrophenyl)ethyl, 2-(4-cyanophenyl)ethyl
$R^2$ = isopropyl, ethyl, methyl
$R^3$ = isopropyl, ethyl, methyl
Reporter = signal-generating reporter unit In the 1-step process, a linker system of the 2-(4-aminophenylsulfonyl)ethyl type is preferred, other cleavable linkers with which a person skilled in the art is familiar being also usable. The use of 2-(4-aminophenylsulfonyl) ethanol permits by reaction of the amino function with signal-generating reporter groups which carry a sulfonyl or carboxyl group access to almost all known signal-generating reporter groups.

In the 2-step process (see FIG. 6), the reporter molecule (e.g. fluorescence tag) and the cleavable linker (e.g. sulfonylethyl linker) are parts of two different chemical molecules.

It is preferred to use phosphate units having cleavable units as linkers in the 2-step process. The linkers (hereinafter: L) preferably have a protected hydroxyl or amino function (hereinafter: H) for the attachment of the next phosphate unit. Suitable hydroxyl or amino protecting groups (hereinafter: G) are known to the person skilled in the art and are e.g. acid-labile (e.g. dimethoxytrityl, monomethoxytrityl), base-labile (e.g. Fmoc) or photo-labile (e.g. MeNPOC, NPPOC). The linker also contains a unit cleavable by an acid, base or by light (hereinafter: X), e.g. sulfonylethyl, 2-(2,2-dicarboxyethyl)propyl, 2-(2-nitrophenyl)propyl, 2-(2-nitrophenyl)ethyl). The linker also contains a spacer (hereinafter: M) which spatially separates the cleavable unit (X) from the amino or hydroxyl function (H). Therefore, linker (L) can be represented by the following general formula:

wherein
X=cleavable unit
H=hydroxyl or amino
G=protecting group for H
M=alkyl, aryl, etc.

The linker is connected to a phosphite amide unit. The resulting linker phosphoramidite reagent is then fused to the oligomer array as described above. The linker phosphoramidite reagent comprises preferably the following general formula:

L = protected cleavable linker (see above)
$R^1$ = phosphate protecting group, e.g. β-cyanoethyl, 2-(4-nitrophenyl)ethyl, 2-(4-cyanophenyl)ethyl
$R^2$ = isopropyl, ethyl, methyl
$R^3$ = isopropyl, ethyl, methyl Preferred linker-phosphoramidite compounds in the 2-step process are:
2-[2-(4,4'-dimethoxytrityloxy)ethylsulfonyl]ethyl-(2-cyanoethyl)-(N,N-diisopropyl)phosphoramidite (Eurogentec, Liege, Belgium)

[3-(4,4'-dimethoxytrityloxy)-2,2-dicarboxyethyl]propyl-(2-cyanoethyl)-N,N-diisopropyl)phosphoramidite A preferred embodiment of the 2-step process is described in FIG. 6. The linker-phosphoramidite reagent (e.g. 2-[2-(4, 4'-dimethoxytrityloxy)ethylsulfonyl]ethyl-(2-cyanoethyl)-(N,N-diisopropyl)phosphoramidite) is first fused to the oligomer array. Following oxidation to produce a stable phosphate bond (and possible capping to prevent uncontrolled chain extensions) and removal of the employed terminal protecting group (e.g. the dimethoxytrityl group by acid treatment), a reporter group (e.g. a Cy5 group derivatized with phosphoramidite=Cy5-phosphoramidite; Pharmacia company) is fused to the cleavable linker unit. Following oxidation to form a stable phosphodiester bond, the array is scanned (e.g. by fluorescence scanning) to identify the previously attached reporter group. Splitting off the linker (e.g. by base treatment in the case of the sulfonylethyl linker) the reporter group is removed in the same step. The phosphate protecting groups may preferably, but not necessarily, be removed in the same step or later. A phosphate unit is left as an attachment at one end of the respective oligomer strand. The array can then be used in standard experiments (e.g. in hybridizations).

The method can be applied to any oligomer arrays of oligonucleotide/nucleic acid biopolymers, e.g. from DNA, RNA and/or analogs thereof. Analogs are understood to mean, e.g. phosphorus thioates, PNA, modified DNA or RNA nucleic acids (e.g. 2'-O-methyl) or also other nucleic acid types having a modified backbone or sugar (e.g. pRNA, homo-DNA, alphapara-NA) or the chimeras thereof. The reporter group-labeled phosphoramidite can also be reacted with the N-terminal end of peptides/proteins and be used as described above.

The quality is controlled e.g. in a fluorescent reporter group by evaluating the solid carrier on which the labeled oligomer grid is disposed using a reader suitable for this dye (e.g. fluorescence microscope, fluorescence scanner). For this purpose, the reader determines for all oligomer positions a relative intensity value which corresponds to the relative amount of synthesized oligomer at this position. A comparison of the determined relative intensities with respect to one another permits a quantitative comparison of the respective occupation with oligomers at all sites of the carrier and/or furnishes information on the quality of the synthesized oligomer grid. This comparison of the relative intensities at the various positions of the grid permits as a sequential step (evaluation of a hybridization experiment of the oligomer chip with probes) a safe comparison of the intensities which result in this case. For example, when during the quality check for a certain position the oligomer concentration measured with respect to another is low, it is also only possible as according to expectations to determine for this position an intensity reduced relative to others when this chip is used in a hybridization experiment.

Having concluded the quality control, the reporter group is split off again. In the case of reporter groups which are bound via a sulfonylethyl-like system to the phosphorus/phosphate groups, this is effected by a treatment using a strong base, e.g. DBU, ammonia, DBN, diisopropylethylamine.

The method can be automated and is therefore suitable for mass screening or great chip charges.

The invention is explained in more detail by means of the following examples.

EXAMPLES

Example 1

Figure 1:
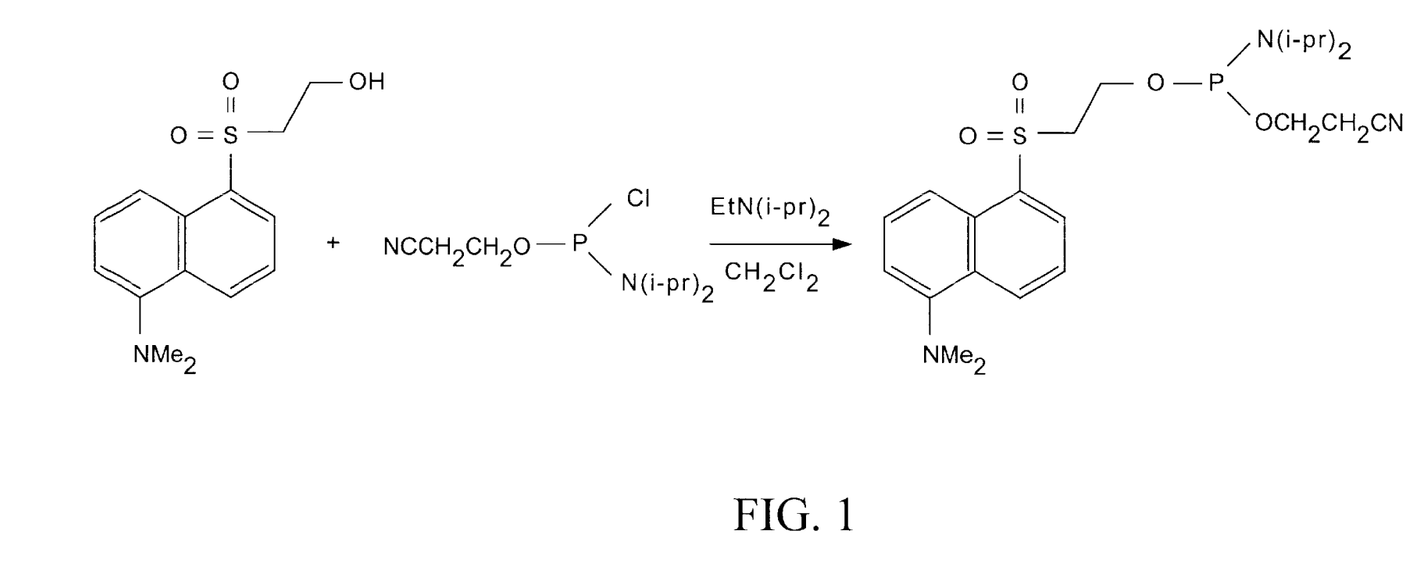
FIG. 1 shows the production of phosphoramidite (2-cyanoethyl-2-dansylethyl-N,N-diisopropyl) phosphoramidite).
Figure 2:
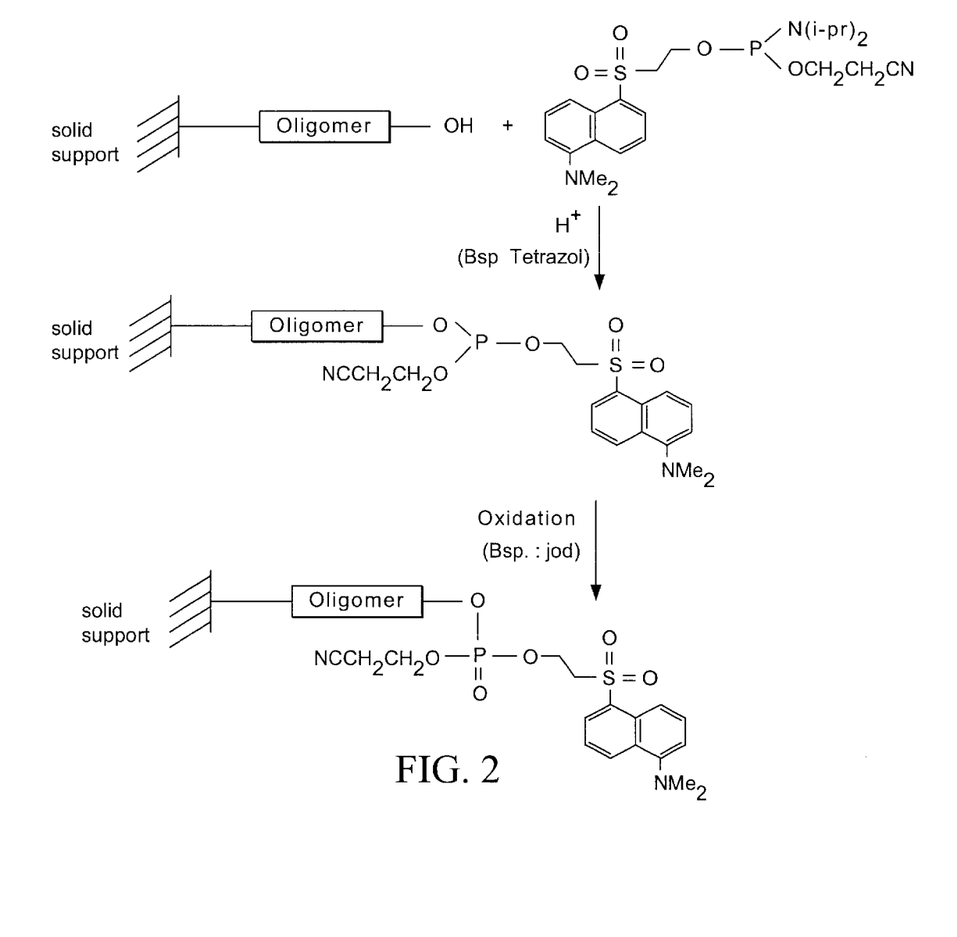
FIG. 2 shows the coupling of the phosphoramidite to the oligomer.

Quality Control of an Oligomer Chip a) Production of (2-cyanoethyl-2-dansylethyl-N,N-diisopropyl)phosphoramidite 4.83 g 2-dansylethanol (17.3 mmol) and 5.92 ml diisopropylethylamine (34.6 mmol) are dissolved in 30 ml anhydrous dichloromethane and cooled in an ice bath. Then, 4.5 g chloro-(2-cyanoethoxy)diisopropylaminophosphane (19.0 mmol) are slowly added. The ice bath was removed. Stirring was continued until TLC showed complete reaction. The reaction mixture was extracted with a saturated sodium bicarbonate solution and dichloromethane, the organic phase was dried over sodium sulfate and evaporated. The resulting oil was purified by means of flash chromatography (50 g SiO2; toluene/ethyl acetate; 0–20% ethyl acetate). 5.7 g of the product were obtained as a fluorescent oil. The yield was 69%. The reaction scheme is shown in FIG. 1.

b) Coupling of the (2-cyanoethyl-2-dansylethyl-N,N-diisopropyl)phosphoramidite to the Oligomer The coupling was effected automatically by means of a DNA synthesizer. For this purpose, the fluorescence-labeled phosphoramidite is dissolved in analogy to a "normal" nucleoside building block (phosphoramidite) in dry acetonitrile (0.5 molar) and is applied by condensation to the already existing oligomers in the solid phase. This is done by means of tetrazole. What is called a capping step (e.g. reagent acetic anhydride with acetylating catalyst N-methylimidazole) usually takes place after the condensation on the DNA synthesizer to prevent uncontrolled further growth of the oligomer chain. This step is not necessary here but is not an impediment either, since the oligomer chain growth has in any case been concluded by the fluorescence-labeled phosphoramidite. The subsequent oxidation step is important which converts the unstable phosphorus(III) group into a stable phosphorus(V) compound. For this purpose, an iodine/pyridine/THF/water mixture is used. The DNA chip fluorescence-labeled in this way is now immediately available for the qualitative checking by a suitable array reader. The reaction scheme is shown in FIG. 2.

c) Carrying out the Quality Control

Figure 3:
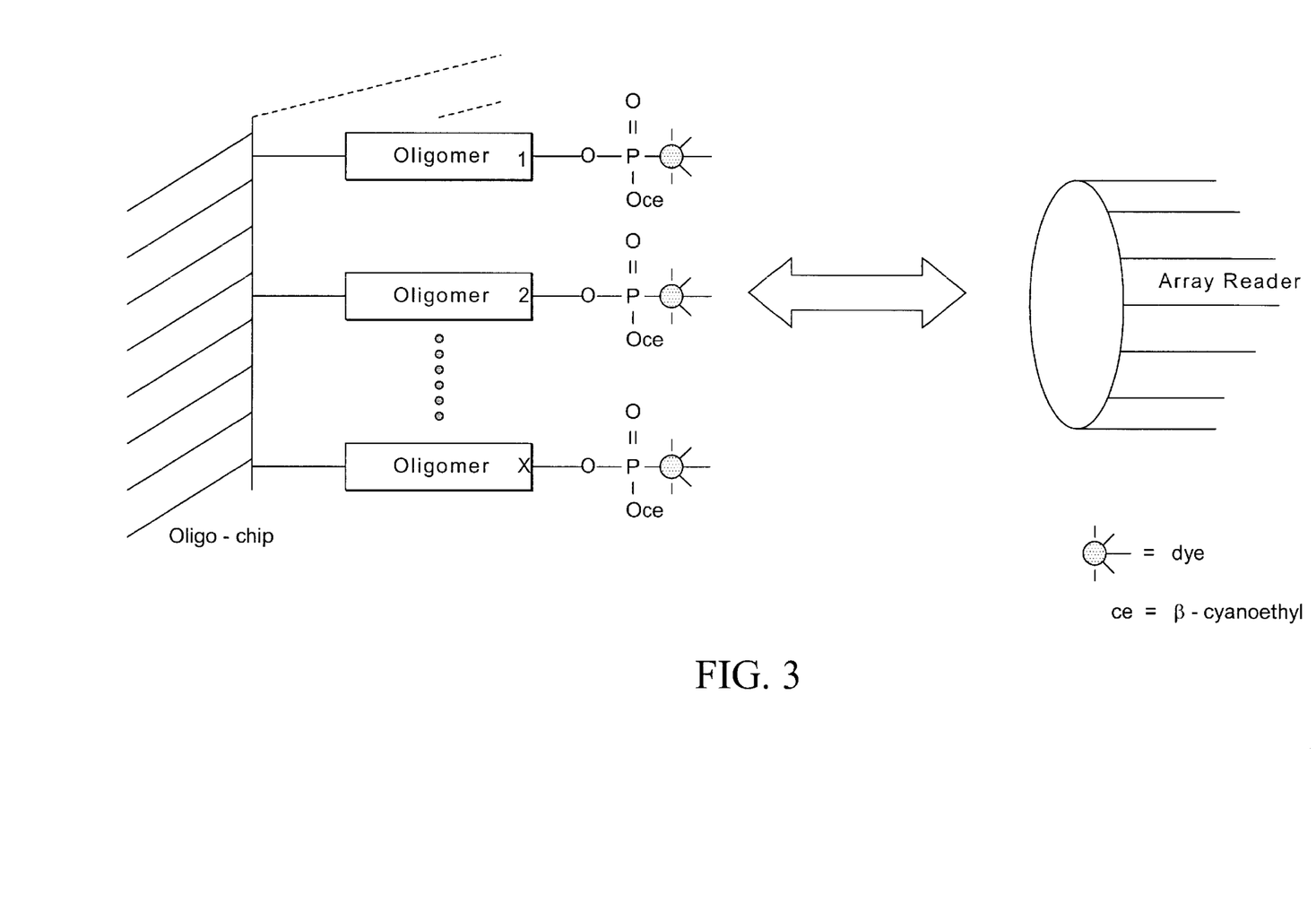
FIG. 3 shows the carrying out of the quality control.

The quality is controlled directly after step (b). Here, fluorescence is stimulated by irradiation of the chip with a wavelength suitable for the dye (dansyl: 350 nm). The emission of the fluorescence (dansyl: 510 nm) is then read by a suitable reader (fluorescence microscope or fluorescence scanner) for each position of the chip and quantified (typically gray-scale values). For example, if no fluorescence is detectable at a certain grid position although an oligomer sequence should be constructed there, it can be concluded that the synthesis was not successful at this position. This chip should then be discarded. By comparing the measured intensities the amount of the oligomers synthesized at this position can be inferred. This may be considered for the use of the oligomer chip in hybridization experiments. In this way, a quality profile can then be prepared for each individual chip by the relative fluorescence intensities of all grid positions (e.g. by way of an excel table). This is a corresponding help for the user to evaluate his hybridization experiments. The reaction scheme is shown in FIG. 3.

d) Splitting-off of the Dansyl Compound

Figure 4:
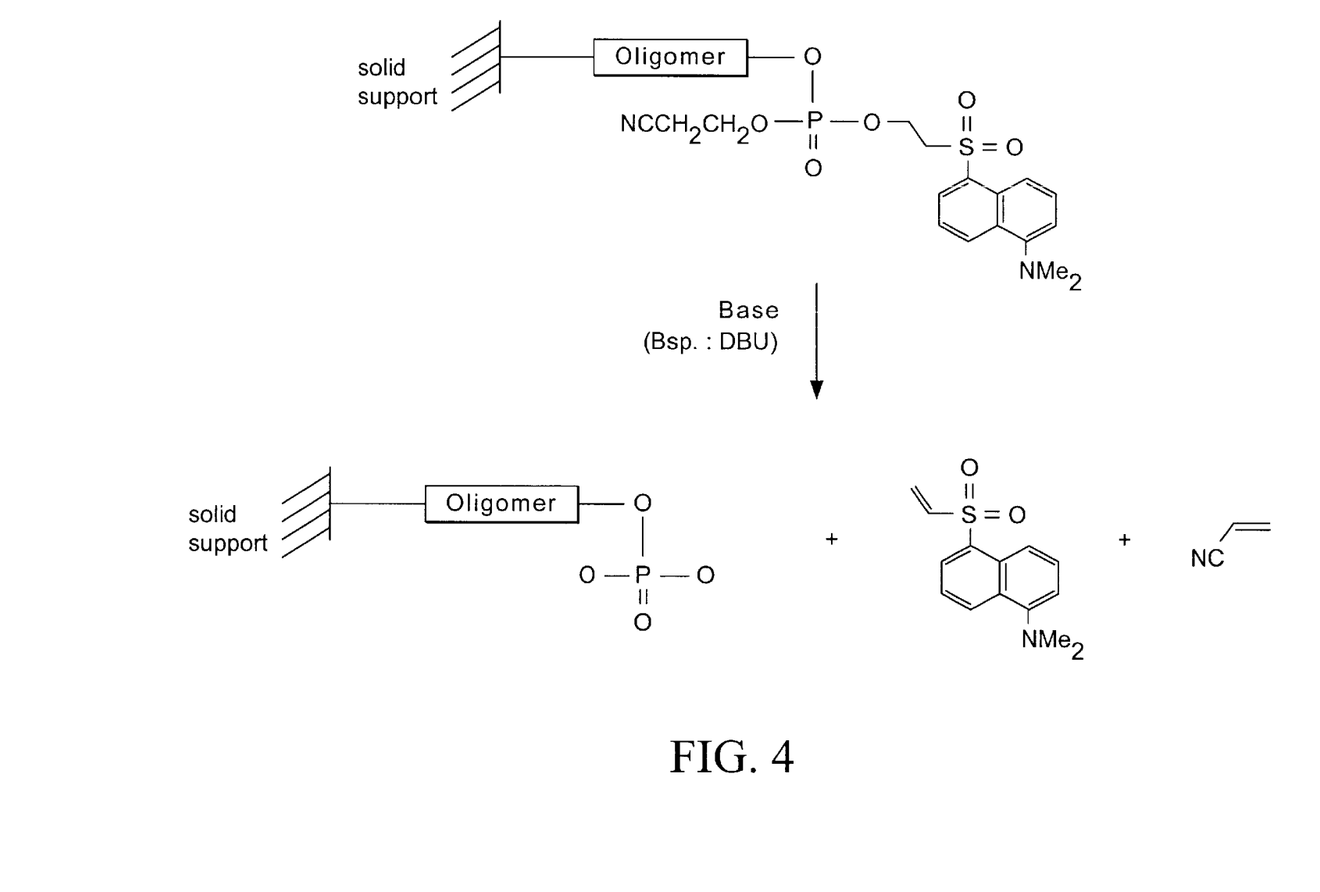
FIG. 4 shows the splitting-off of the reporter group.

Having concluded the quality check, the dansyl compound can be abstracted again by treatment with a strong base, e.g. DBU or DBN. This is usefully done by rinsing the oligomer chip in the base. In the case of the above-mentioned dansyl dye and using 1 M DBU in acetonitrile, this result is already obtained after 1 to 2 min. at the latest. The á-cyanoethyl phosphate protecting group is split off simultaneously with the splitting-off of the dansyl residue. The residues (styrene derivatives) of the dansyl groups and the cyanoethyl groups remain in the basic solution and can simply be washed away. The DNA chip is available for the aspired use immediately after the splitting-off and washing step (e.g. hybridization experiments). The phosphate grouping remaining at the oligomer additionally increases advantageously the temperature at which the hybridization experiments may take place. The reaction scheme is shown in FIG. 4.

What is claimed is:

1. A method for controlling the quality of an oligonucleotide array, comprising the steps of:

fusing a phosphate unit linked to a signal-generating reporter group to oligonucleotides bound at selected or all grid positions of an oligonucleotide array, determining the degree of oligomer synthesis by means of the signal of the reporter group attached to the oligonucleotides at the grid positions, preparing a quality control profile of the grid positions, and splitting off the reporter group.

2. The method according to claim 1, wherein the oligonucleotides are DNA, RNA or analogs thereof.

3. The method according to claim 1 or 2, wherein the reporter group is a fluorescent, coloring, radioactive, or chemiluminescent group.

4. The method according to claim 1 or 2, wherein the reporter group is split off under basic conditions.

5. The method according to claim 3, wherein when a fluorescent group is used, the signal of the reporter group is determined by fluorescence microscopy or fluorescence scanner.

6. The method according to claim 1 or 2, wherein the phosphate unit and the reporter group are linked by a linker.

* * * * *